(12) United States Patent
Williams et al.

(10) Patent No.: US 8,384,136 B2
(45) Date of Patent: Feb. 26, 2013

(54) DEMULTIPLEXED NANOWIRE SENSOR ARRAY FOR DETECTION OF CHEMICAL AND BIOLOGICAL SPECIES

(75) Inventors: R. Stanley Williams, Redwood City, CA (US); Philip J. Kuekes, Menlo Park, CA (US); Yong Chen, Sherman Oaks, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1006 days.

(21) Appl. No.: 11/584,028

(22) Filed: Oct. 19, 2006

(65) Prior Publication Data

US 2008/0094051 A1 Apr. 24, 2008

(51) Int. Cl.
*G01R 19/00* (2006.01)

(52) U.S. Cl. ............ 257/252; 257/253; 435/4; 977/700; 977/712; 977/762

(58) Field of Classification Search ...... 435/4; 257/253, 257/252; 977/700, 712, 762; 438/4; *G01R 19/00*
See application file for complete search history.

(56) References Cited

U.S. PATENT DOCUMENTS

| | | | | |
|---|---|---|---|---|
| 5,670,322 A * | 9/1997 | Eggers et al. | ................ | 506/3 |
| 5,846,708 A * | 12/1998 | Hollis et al. | ................ | 506/12 |
| 6,256,767 B1 * | 7/2001 | Kuekes et al. | ................ | 716/9 |
| 7,256,466 B2 * | 8/2007 | Lieber et al. | ................ | 257/414 |
| 7,310,004 B2 * | 12/2007 | DeHon | ................ | 326/41 |
| 7,385,267 B2 * | 6/2008 | Lieber et al. | ................ | 257/414 |
| 7,410,904 B2 * | 8/2008 | Stasiak et al. | ................ | 438/700 |
| 7,575,933 B2 * | 8/2009 | Gabriel et al. | ................ | 436/151 |
| 2002/0117659 A1 * | 8/2002 | Lieber et al. | ................ | 257/14 |
| 2002/0165675 A1 * | 11/2002 | Golovlev | ................ | 702/27 |
| 2004/0041617 A1 * | 3/2004 | Snider et al. | ................ | 327/365 |
| 2004/0192072 A1 * | 9/2004 | Snow et al. | ................ | 438/800 |
| 2004/0214447 A1 * | 10/2004 | Stasiak et al. | ................ | 438/710 |
| 2005/0055387 A1 * | 3/2005 | Kuekes et al. | ................ | 708/1 |
| 2005/0070802 A1 * | 3/2005 | Peters et al. | ................ | 600/459 |
| 2005/0266455 A1 * | 12/2005 | Golovlev | ................ | 435/6 |
| 2006/0078468 A1 * | 4/2006 | Gabriel et al. | ................ | 422/88 |

OTHER PUBLICATIONS

Zheng et al., Multiplexed electrical detection of cancer markers with nanowire sensor arrays, Nature Biotechnology, vol. 23, No. 10, p. 1294-1301, Oct. 2005.*

* cited by examiner

*Primary Examiner* — Peniel M Gumedzoe
(74) *Attorney, Agent, or Firm* — David W. Collins (57) ABSTRACT

A demultiplexed nanowire sensor array for detecting different chemical and biological species are provided, comprising a sensor array and a demultiplexer array. Methods of detecting at least two chemical and/or biological species are also provided, using the demultiplexed nanowire sensor array.

10 Claims, 7 Drawing Sheets

FIG. 1

- PRIOR ART -

DEMULTIPLEXED NANOWIRE SENSOR ARRAY FOR DETECTION OF CHEMICAL AND BIOLOGICAL SPECIES

BACKGROUND ART

The present invention is directed to sensors, and, more particularly, to nanoscale sensor arrays for detecting multiple different chemical and biological species.

Prior art demultiplexers are well known, as are nanoscale wire sensors. However, the detectors described in the prior art require active circuitry to measure the current flowing through each wire. This means that each semiconductor wire must have its own measurement circuitry, which is expensive, and it also severely limits the density at which detector wires can be integrated onto a sensing platform.

The prior art sensors have demonstrated high sensitivity to chemical and biological species, and are based on converting a chemical quantity into electrical signals. As one example of a well-known device, a crossed-wire device comprises two wires and an active material sandwiched therebetween. When a chemical or biological species is absorbed onto the active material, it will change the electrical properties in the device.

The active material can be a semiconductor, a dielectric material (e.g., an oxide), a polymer, a molecule, etc. The device can be a resistor, a capacitor, a diode, a transistor, etc. Such materials and devices have been described elsewhere.

The problem for such sensors is that the change of the electrical properties only rely on the interaction between the active material and the species; usually, one kind of active material is only sensitive to one or a few species, so that such a sensor can only detect one or a few species. Alternatively, such sensors may detect too many species and not be able to distinguish between them.

It would be desirable to sense a large number of species and read out the electrical signals associated with the detection of such species.

SUMMARY

In accordance with the embodiments disclosed herein, demultiplexed nanowire sensor arrays for detecting different chemical and biological species are provided. Methods of detecting at least two chemical and/or biological species are also provided.

DETAILED DESCRIPTION

Reference is made now in detail to specific embodiments for practicing the invention.

A demultiplexed nanowire sensor array is disclosed and claimed herein for detecting different chemical and biological species. The demultiplexed nanowire sensor array comprises a sensor array and a demultiplexer. In some embodiments, the sensor array comprises (a) a first set of nanowires crossing a second set of wires at a non-zero angle to form an array of cross points, or switches, and (b) an active material at least at each cross point. The active material at a cross point is alterable at that cross point, or switch, by a different receptor. Each receptor is specific to detecting a specific chemical or biological species. The demultiplexer addresses the nanowires and permits measurement of the electrical resistance of each wire. The value of the electrical resistance may be used to identify the species.

In other embodiments, the demultiplexed nanowire sensor array comprises a sensor array. The sensor array comprises a first set of semiconductor nanowires, at least one gate operatively associated with said set of nanowires, and each nanowire is functionalized differently from another nanowire. The gate has two edges configured with one said edge on one side of said set of nanowires and with a second said edge on another side of said set of nanowires. The demultiplexed nanowire sensor array further includes bias voltage means for applying a bias voltage to each edge, with the bias voltage applied to the first edge the same or different than the bias voltage applied to the second edge. The demultiplexed nanowire sensor array further includes at least one demultiplexer for addressing the nanowires and permitting measurement of electrical resistance of each nanowire.

Two embodiments of the demultiplexed nanowire sensor array are specifically described, one in which the switches are normally open and one in which the switches are normally closed. Within each embodiment, a nanowire sensor array for identifying different chemical and biological species is provided, along with a demultiplexer for demultiplexing and reading the nanowire array.

Switches Normally Open

A1. Nanowire Sensor Array

The nanowire array is used to identify different chemical and biological species. In this first type of sensor array, the receptors are on the side of a nanowire forming part of a nanowire switch (comprising two wires crossing at a non-zero angle). Both wires are electrical conductors (e.g., metals or semiconductors), with one wire (the sensor) being a nanowire and the other wire (the demultiplexer) being either a nanowire or a microwire. In this case, the switch is normally open (without any molecules present) and is closed when a chemical or biological species is adsorbed thereon.

As used herein, "nano" refers to functional dimensions of about 1 to 100 nm, while "micro" refers to functional dimensions of about 0.2 to 10 µm.

Figure 1:
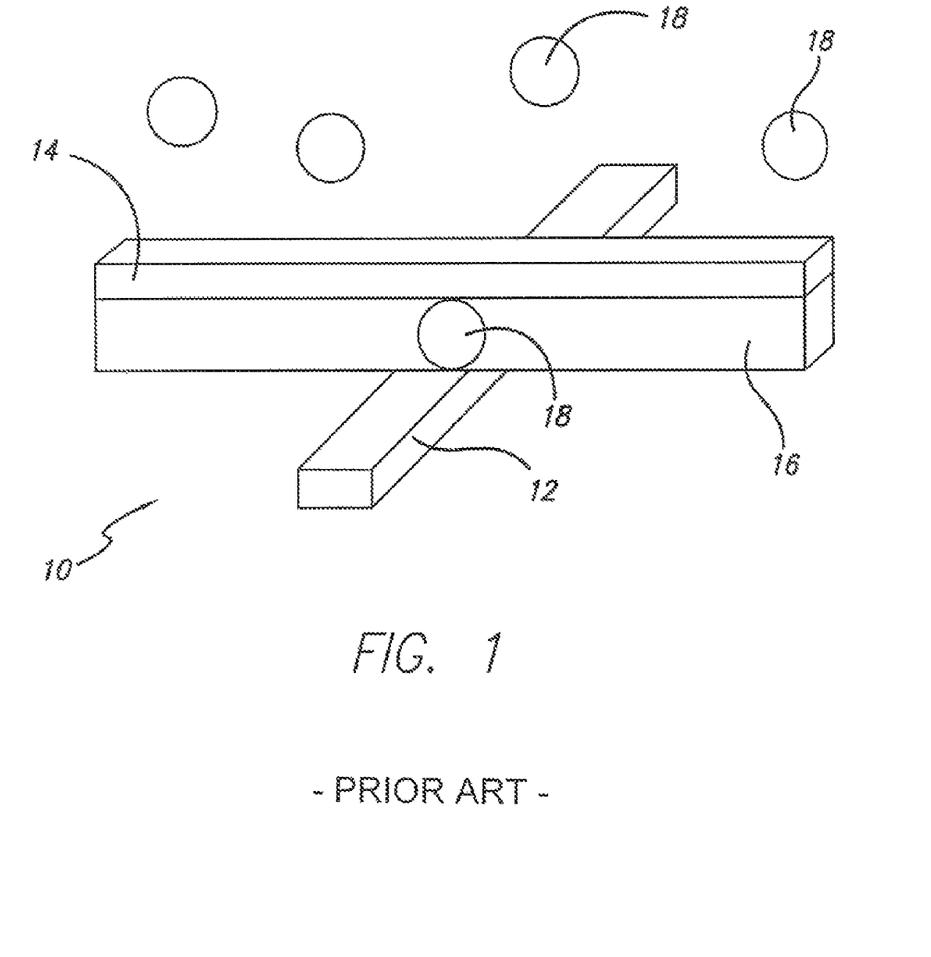
FIG. 1 is a schematic diagram, depicting an exemplar crossed-wire device for detecting one or a few chemical/biological species.

Prior art sensors have demonstrated high sensitivity to chemical and biological species; such prior art sensors are capable of converting a chemical quantity into an electrical signal. A chemical/biological sensor for detecting one or a few species, as depicted in FIG. 1, typically comprises a crossed-wire device 10 comprising two metal wires 12, 14 and an active material 16 sandwiched therebetween. When a chemical or biological species 18 is absorbed onto the active material 16, it will change the electrical properties in the device 10.

In order to create a sensor that can detect many different species (such as a DNA section with different sequences or different chemicals), a sensor array with a crossbar structure may be employed, in which each cross point can be addressed as a device (resistor, capacitor, diode, or transistor) independently with logic demultiplexers associated with it.

Previously, it has been demonstrated that such a crossbar circuit can be used as a memory circuit; see, e.g., U.S. Pat. No. 6,128,214, entitled "Molecular Wire Crossbar Memory", issued on Oct. 3, 2000, to Philip J. Kuekes et al. Access to individual crossed-wire junctions is achievable with a demultiplexer, such as taught in U.S. Pat. No. 6,256,767, entitled "Demultiplexer for a Molecular Wire Crossbar Network (MWCN DEMUX)", issued on Jul. 3, 2001, to Philip J. Kuekes et al. The contents of the foregoing patents are incorporated herein by reference, and their teachings are used to construct the sensor disclosed herein.

Figure 2A:
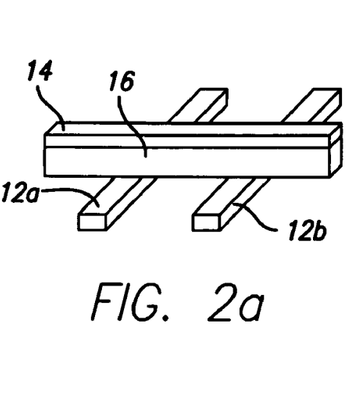
FIGS. 2a-2f are each a schematic diagram of an embodiment for detecting multiple chemical/biological species or analytes.

To make a sensor array, a crossbar circuit can be fabricated with, for example, two sets of parallel nanowires 12a, 12b crossing a third nanowire 14 at a non-zero angle, with a layer of active material 16 sandwiched between them (FIG. 2a). One can selectively apply a voltage (or current) between wires 12a and 14 (FIG. 2b) that attracts one kind of receptor 120 as it flows around the sensor array, so the receptor will be absorbed only on the side of the active material 16 near the cross point between wires 12a and 14.

Figure 2B:
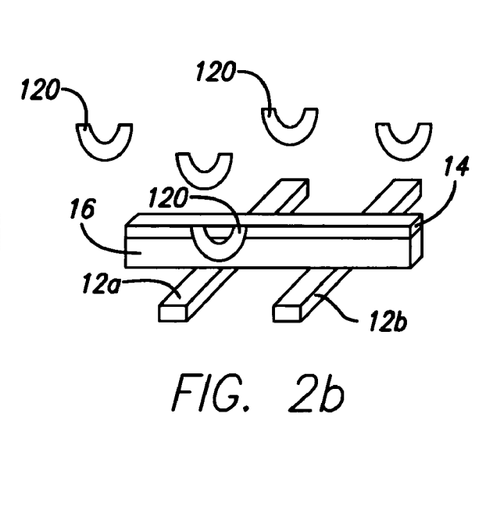

The adsorption may be done through a chemical or electrochemical method. For example, a strong electrical field can be used to attract a receptor to a cross point. The presence of dipoles on the receptor 120 may be attracted by the electric field between wires 12a and 14. In another embodiment, photolinking may be used to attach receptors 120 at high electric field areas (e.g., photolinker moieties on the receptor or catalyst-bearing photolinker moieties), by exposure of the photolinker moieties to photons.

Figure 2C:
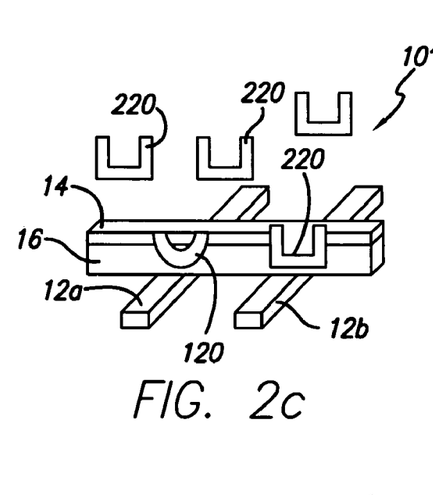

The same sequence can be repeated between wires 12b and 14 (FIG. 2c) when a different kind of receptor 220 flows around the sensor array, so the second receptor will be absorbed only by the active material 16 near the cross point between wires 12b and 14. In such a manner, a nanowire sensor array 10' is formed that is capable of detecting at least two (as shown here), and preferably a plurality, of chemical and/or biological species. Detection of additional chemical and/or biological species is achieved by adding more nanowires and receptors in accordance with the foregoing teachings, where such additional nanowires cross nanowire 14.

Figure 2D:
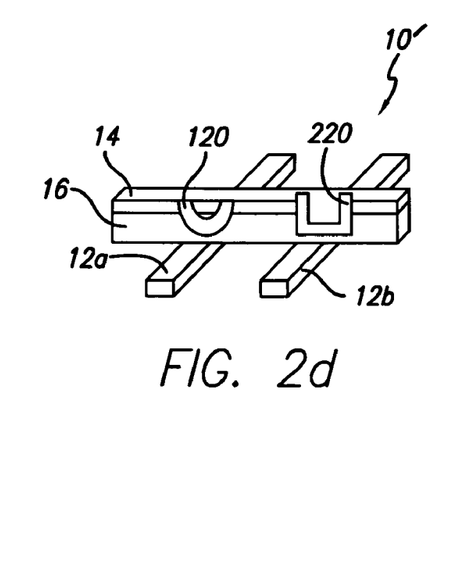
Figure 2E:
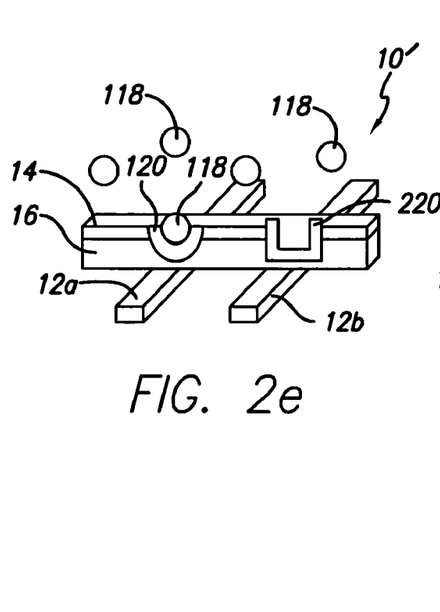

The number of wires in a crossbar can be extended from 2 to $10^3$ or even larger. With selective absorption of different receptors 120, 220 at different cross points, the crossbar sensor array can be ready to detect many different species (FIG. 2d). When one kind of species 118 flows around the sensor array 10' (as shown in FIG. 2e), it will only be absorbed by its corresponding receptor 120 at the cross point between wires 12a and 14, and change the electric properties of the device between wires 12a and 14. When a different kind of species 218 flows around the sensor array 10' (FIG. 2f), it will only be absorbed by its corresponding receptor 220 at the cross point between wires 12b and 14, and change the electric properties of the device between wires 12b and 14. By monitoring the change of the electric properties of the devices at different cross points in the crossbar (with a demultiplexer for circuits with a large number of wires), one can efficiently distinguish large amount of different species in an environment.

In the nanowire sensor array 10', the first set of nanowires (12, 12a, 12b, etc.) and the second set of nanowires (14, etc.) may comprise metal-metal or metal-semiconductor or semiconductor-semiconductor sets. For metal nanowires, the metals are selected from the group consisting of Ag, Pt, Au, Pd, Ti, Al, Cr, Cu, etc. For semiconductor nanowires, the semiconductors are selected from the group consisting of Si, Ge, GaAs, etc.

The active material 16 used in the nanowire sensor array 10' may be selected from the group consisting of semiconductors, polymers, and molecules. In the case of semiconductors, the same materials as listed above may be used (although the specific material selected would be different than that of either nanowire). The presence of an analyte/receptor complex induces conductivity on the surface of the semiconductor. For polymers, organic compounds that can immobilize the analyte and detect the change of analyte by some electrical property may be used; examples include, but are not limited to, poly-lactic acid-co-glycolic acid (PLAGA), and polypyrrole. Molecules have the same properties as the polymers; examples include, but are not limited to, enzymes and antibodies. In the case of polymers and molecules, the analyte/receptor complex essentially dopes these materials, rendering them more conductive. An increase in the conductivity between a wire 12 and wire 14 results in effectively closing a switch at that junction.

One can measure (or sense) the absorbed analytes in different ways. For example, in a potentiometric method, measurement of a cell voltage may be done at zero current. As another example, in a voltammetric method, an increasing potential is applied to the cell until oxidation (or reduction) of the analyte(s) occur(s).

The active material 16 is typically present at each cross point, and may, in fact, extend beyond each cross point. The number of receptors 120, 220 may be equal to the number of cross points or be some number less than the number of cross points.

The present embodiments are directed to a nanowire sensor array that utilizes a set of nanoscale wires for measuring the presence of adsorbed or activated species on the wire surface. The advantage of this approach over previous wire sensors is that this approach allows addressing and reading of a large number of wires in order to identify various adsorbed species.

For example, ionophores are the most useful type of ion-selected (polymer) materials that can be used as active materials. Polymer membranes, incorporating valinomycin crown ethers have been used successfully to detect $K^+$, $Na^+$, $Ca^{2+}$, etc. An example for a suitable receptor is oestrogen, some of which are strongly oestrogenic, such as 17-β-oestradiol, while others are weaker, such as the oestrogenic mimics. A sensor based on such an acceptor will not respond equally to all oestrogenic compounds, but will give an indication of the extent of the oestrogenic activity.

A2. Demultiplexer

Figure 3:
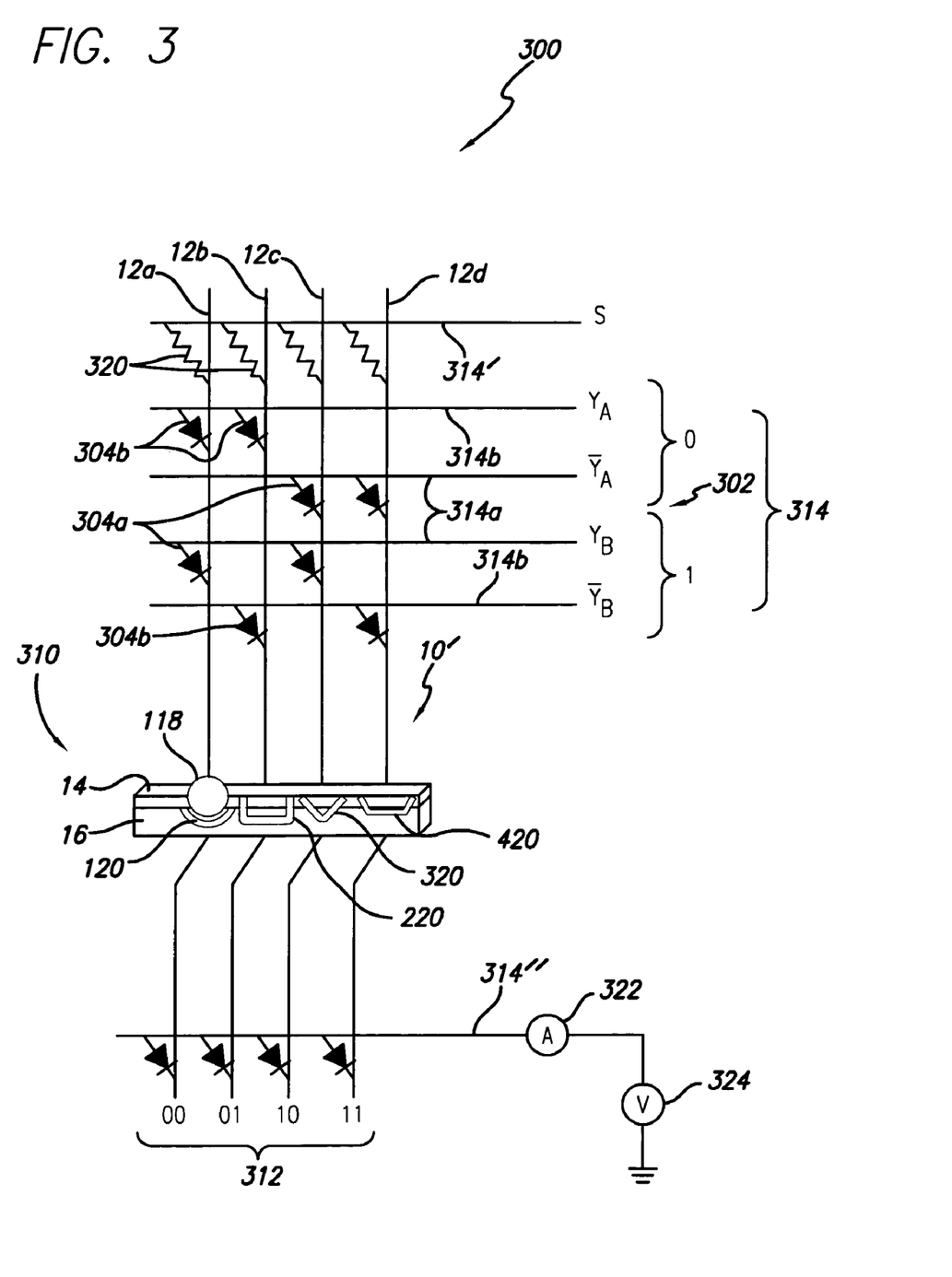
FIG. 3 is a schematic diagram, generally showing an embodiment of a wire sensor array that is demultiplexed and read using a diode-logic demultiplexer that may be used in conjunction with the device of FIGS. 2e-2f for detecting multiple chemical/biological species, employing switches that are normally open.

FIG. 3 shows a schematic diagram of one embodiment of a demultiplexed nanowire sensor array 300, comprising a wire sensor array 310 and a demultiplexer 302. The wire sensor array 310 comprises a set of parallel electrically conducting (nano)wires (vertical wires 312) that are addressed using a diode-logic demultiplexer 302 (horizontal wires 314) so that the resistance of each individual wire or various groups of wires can be measured. It will be appreciated that the designations "vertical" and "horizontal" are not meant to denote actual placement in space, but rather are used as relative terms to denote relationship to each other. The vertical wires 312 may be separated by nanoscale dimensions.

In particular, FIG. 3 illustrates a schematic diagram, showing a wire sensor array 310 that is demultiplexed by a nanowire sensor array 302 and read using a diode-logic multiplexer 314".

Figure 2F:
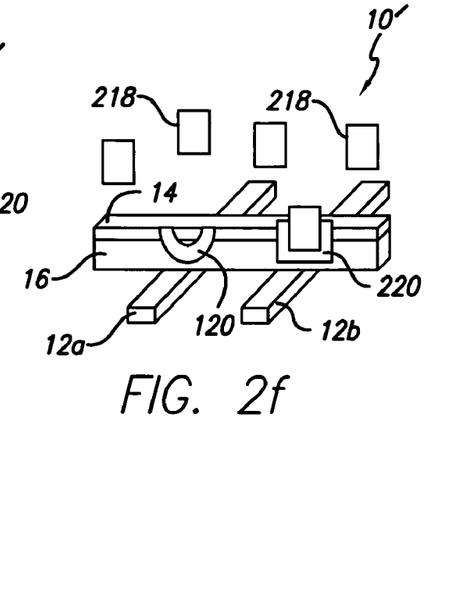

The wire sensor array 310 is an extension of the configuration depicted in FIG. 2f. There, two different sensors 120, 220 are shown. The number of sensors, however, is not limited to two, and may, in fact, be any number that can be configured to uniquely detect a chemical or biological species. In FIG. 3, the wire sensor array 310 comprises four sensors, 120, 220, 320, 420.

While a diode-logic demultiplexer 302 is shown in FIG. 3, an FET-logic demultiplexer may alternately be employed. The vertical wires 312 may comprise a semiconductor, and, in some embodiments, may have a width and thickness less than 100 nm. The horizontal wires 314 may comprise a metal.

The wire labeled 314' (the designation S denotes source voltage) may either comprise a different metal than the other horizontal wires 314, or it may be narrower. In some embodiments, the "ohmic" connections between the source wire 314' and the semiconductor wires 312 may have a resistance that is greater than the resistance of the forward-biased diodes connecting the rest of the metal wires 314 to the semiconductor wires, but less than the resistance of the reverse-biased diodes.

Diodes 304a may be connected to wires 314a and are forward-biased, while diodes 304b are connected to wires 314b and are reverse-biased (current flowing from high to low). Resistors 320 may control the current and balance the current so as to enable the selection of just one wire (as an example, wire 314b). The horizontal metal wires 314, 314', 314" can be fabricated using conventional lithographic techniques. In this case, the diodes 304a, 304b may be all of the Schottky type. Wires labeled "a" and "b" may be held at high and low bias voltages, respectively. While a 4×4 array of diodes 304a, 304b is specifically depicted in FIG. 3, the teachings herein extend to an N×M array of diodes, where N and M are integers that may be the same or different and that may each extend to several hundred or more (and even greater for the FET-logic case).

Ammeter A 322 may be used to enable measurement. The particular line 314" associated with the ammeter 322 is a multiplexer. As a result, FIG. 3 depicts a combination multiplexer-demultiplexer.

The measuring is performed as follows: a voltage is applied by a voltage source $V_b$ 324. All current passing through a selected wire, say wire 12b, is measured with the ammeter A 322. Either a single wire 12b is selected by a demultiplexer or by a sub-set of wires. This permits a single measurement for a large number of nanowires. In order to achieve a higher level of defect tolerance or a wider voltage range between high and low voltages in the demultiplexer, one may use a supplemental coded demultiplexer, such as described in patent application Ser. No. 10/659,892, filed Sep. 10, 2003, entitled "Supplemental-Coded Demultiplexer with Resistor Logic" by Philip J. Kuekes et al, published as U.S. Publication No. 2005/0055387 on Mar. 10, 2005, the contents of which are incorporated herein by reference. In this case, an extra pair or pairs of addressing wires may be added to provide a level of defect tolerance through intelligent redundancy and/or to broaden the voltage difference between the high and low state voltages of the demultiplexer, especially in the case of weak diodes or if resistor logic is necessary.

B. Switches Normally Closed—Nanowire Sensor Array and Demultiplexer

In the second type of sensor array, the receptors are on the top of a nanowire forming part of a nanowire switch (as defined above). Here, both wires are semiconductor, with one wire (the sensor) being a nanowire and the other wire (the demultiplexer) being typically a microwire. In this case, the switch is normally closed (without any molecules present) and is open when a chemical or biological species is adsorbed thereon. That is to say, the addition of the species to the switch causes it to open, preventing current from flowing.

Figure 4:
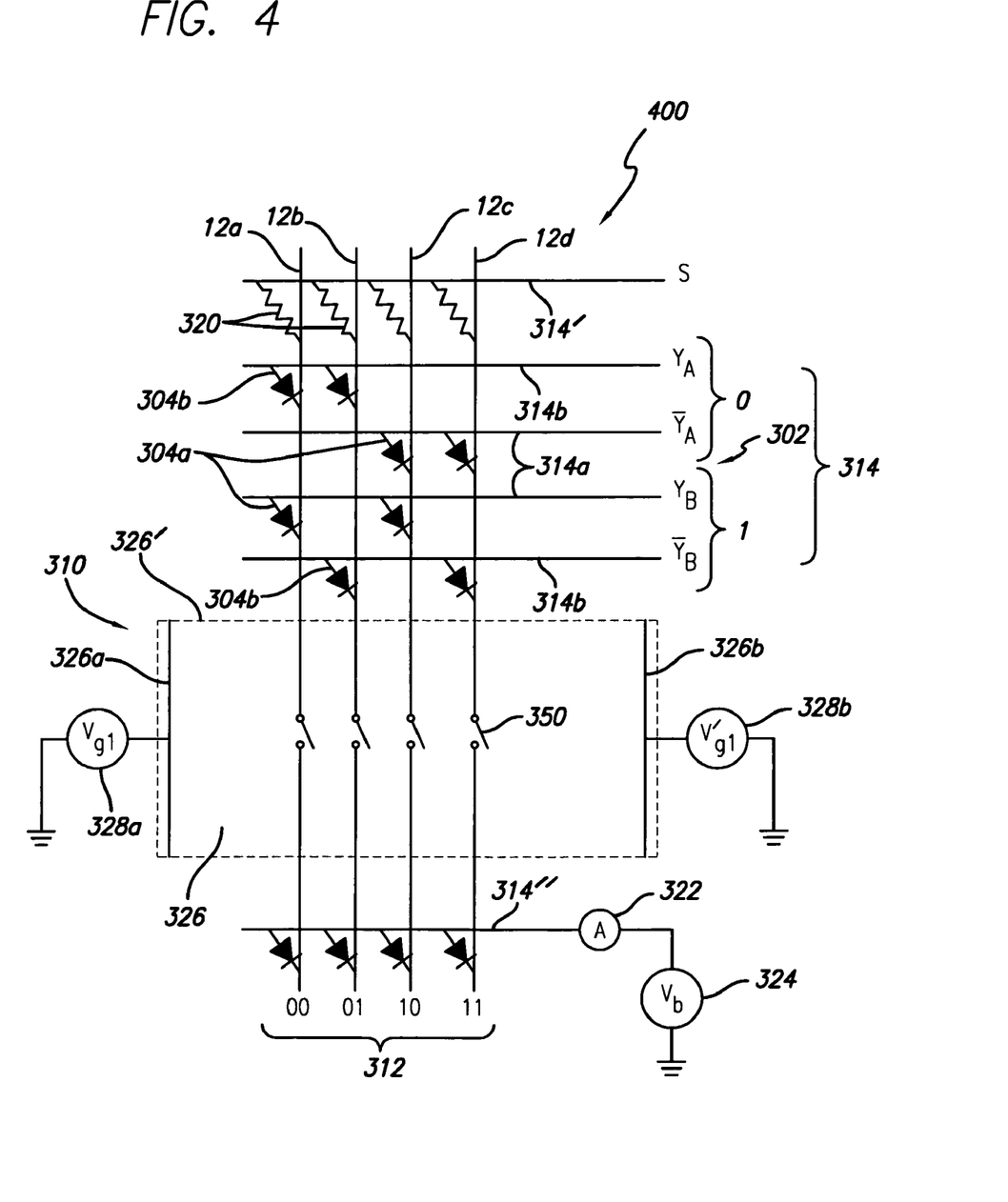
FIG. 4 is similar to FIG. 3, but including further details on a gate which makes each nanowire in the wire sensor array a double gated (chemically gated and electrically gated) FET, wherein a gate voltage allows the sensitivity of the nanowires to be tuned and wherein the switches are normally closed.

FIG. 4 is similar to FIG. 3, but includes further details on a gate which makes each nanowire in the wire sensor array a double gated (chemically gated and electrically gated) FET, wherein a gate voltage allows the sensitivity of the nanowires to be tuned and wherein the switches are normally closed. Also, FIG. 4 has no equivalent for wire 14 (shown in FIG. 3). In FIG. 3, the chemically activated switches (normally open) are between the wires 12 and 14, while in FIG. 4, the chemically activated switches (normally open) are along the wires 12 (see FIGS. 6a-6b, discussed in greater detail below). When there are multiple switches between several wires 14 and a single wire 12 (FIG. 3), then the closing of any single switch allows detection due to a change in voltage on wire 12. Conversely, when there are multiple switches in series along a single wire 12 (FIGS. 4-6), then the opening of any single switch breaks the conduction path along that wire 12.

In the embodiment of the gated nanowire sensor array 400, shown in FIG. 4, the wire sensor array 310 is demultiplexed and read using the diode-logic demultiplexer 314. In this case, all of the wires 312 (here, 12a, 12b, 12c, 12d) are gated, which makes each wire an FET. The gate region 326 lies below the plane of the nanowires 312. The gate voltage allows the sensitivity of the wires 312 to be tuned. This tuning can be used to deplete the nanowires 312 and/or make them respond to different molecular species that adsorb onto the nanowires. By contacting each side 326a, 326b of the gate 326 under the nanowires 312 and applying different potentials, $V_{g1}$ 328a and $V'_{g1}$ 328b, it is also possible to gate each nanowire differently. This makes each nanowire 312 distinct, and therefore reading the state of the different wires provides an additional control that can be used to determine the identity of adsorbed species.

Figure 6:
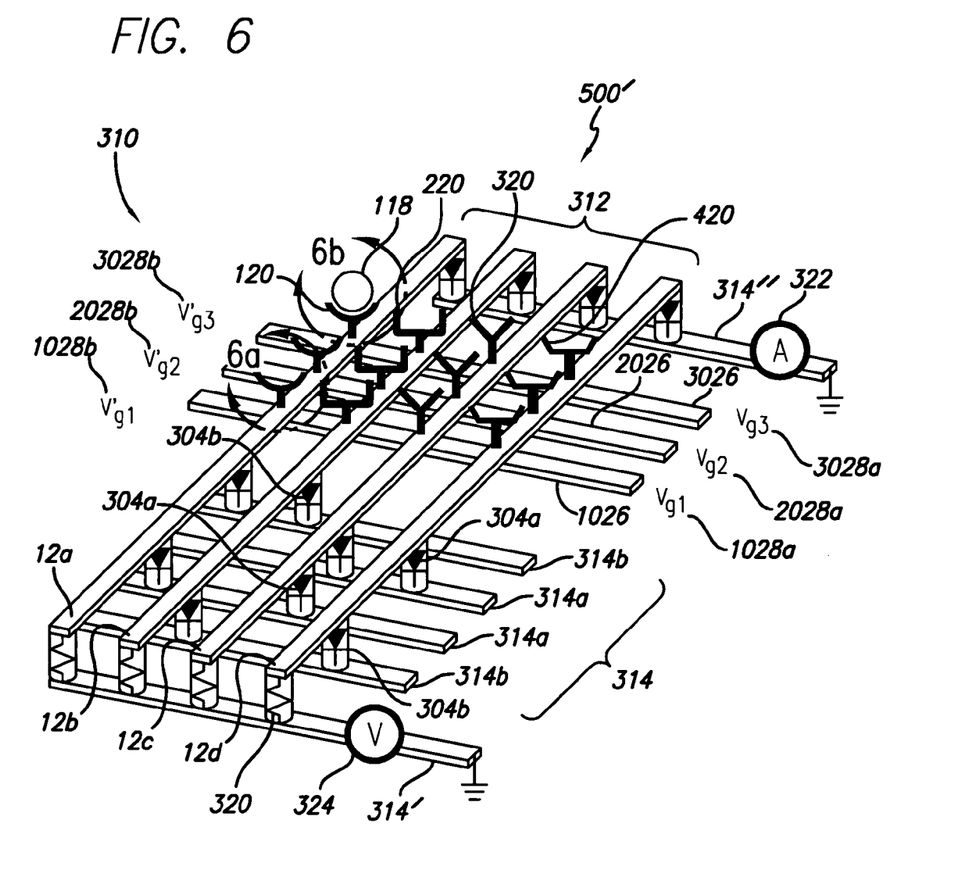
FIG. 6 is a diagrammatic view of an embodiment of FIG. 5.

Each semiconductor wire 312 in the array 310 is distinctly functionalized (as shown in FIG. 6, described in greater detail below) in a manner sufficient to actively bind a chemical or biological species; such functionalization is known in the art and does not form a part of the present teachings; see, e.g., James R. Heath et al, U.S. Pat. No. 6,459,095, issued Oct. 1, 2002. For the case where the wire 312 is intrinsic or doped at a very low level, it is possible for even a single binding event onto a nanowire to contribute substantially to the total doping of the wire. Thus, the conductivity of the wire 312 will increase significantly upon the binding of the species of interest, and the resistance of the wire will decrease. For example, a nanowire measuring 10×10×1000 nm has a total volume of only $10^{-16}$ cm$^3$, so doping a nominally undoped wire 312 may change the conductivity of the wire substantially. For example, the resistivity of non-doped Si can be as high as 1,000 ohm-cm, whereas doped Si (e.g., $10^{19}$ cm$^{-3}$) can be as low as 0.005 ohm-cm. Therefore, there can be potentially six orders of magnitude change by putting 1,000 dopant atoms into a 10×10×1000 nm nanowire, or 1 dopant atom per nanometer length of the wire with a 10×10 nm cross-section.

For the opposite case where the nanowire 312 has some intentional doping, a single binding event can effectively act as a gate and shut off current flow through the wire. These types of switching events caused by the binding of a chemical or biological species to the wire are shown schematically as switches along the length of the wires, which may be several microns long. Thus, the bound molecule acts as a switch. Consequently, switches 350 are shown in the gate 326, which are symbolic of gating action of the molecule(s). The switches 350 are shown open in FIG. 4 (as well as FIG. 5) for clarity, but it will be appreciated that in the absence of a species, the switches are normally closed.

As mentioned previously, the detectors described in the prior art require active circuitry to measure the current flowing through each wire. This means that each semiconductor wire must have its own measurement circuitry, which is expensive, and it also severely limits the density at which detector wires can be integrated onto a sensing platform. The present teachings allow a large number of sensing wires in an array to be controlled by a relatively small amount of active circuitry, which decreases the cost of the platform per sensing wire, and also allows for a much higher integration density of sensor wires. Specifically, each nanowire 312 is spaced at nanoscale dimensions. Sensing wires 314*a*, 314*b* are comparatively few, on the order of log N, where N is the number of nanowires 312. This further decreases the cost per wire, and also greatly increases the total sensitivity of the device, which is directly proportional to the total area of the sensor wires on the platform.

The array 310 can have several different operating modes. In the simplest, the source wire 314' is grounded, as are all of the input wires to the demultiplexer 314, and the current is measured for all of the wires in parallel. In this mode, one needs to have a very sensitive analog detector to determine the relatively small change in the resistance of all the parallel wires when one wire or a few wires are "switched" by the adsorption of a targeted species. This can essentially be a standby mode for the device.

When higher precision readings of the array 310 are required, the address wires of the demultiplexer 314 can be configured with voltages that will select individual wires in the array or groups of wires in the array. By changing the input voltages on the demultiplexer 314, the individual sensor wires or groups of wires can be cycled continuously, and the resistance of each sensor wire or group of wires can be measured and stored for real-time or later analysis. The total concentration of the material can be determined by the rate of adsorption.

A higher level of identification of the particular material being detected can be obtained by having a platform with many sensor arrays, each one with a different agent bound to the semiconductor wires. Analysis of the frequencies of adsorption at the various arrays can provide for improved identification of the species. In addition, the arrays can be systematically heated in various cycles in order to determine characteristic desorption temperatures, which will further aid in identification of the adsorbed species. Analysis of the spatial distribution of adsorption events, either on a single array by examining trends across the wires or by analyzing differential adsorption frequencies at different arrays on a platform, can provide information about the direction of approach of the species of interest.

FIG. 4 described above is directed to an embodiment having one gate 326. The possibility to gate each nanowire 312 differently, as described in greater detail below with reference to FIG. 7, makes each nanowire distinct, and therefore reading the state of the different wires provides an additional control that can be used to determine the identity of adsorbed species.

Figure 5:
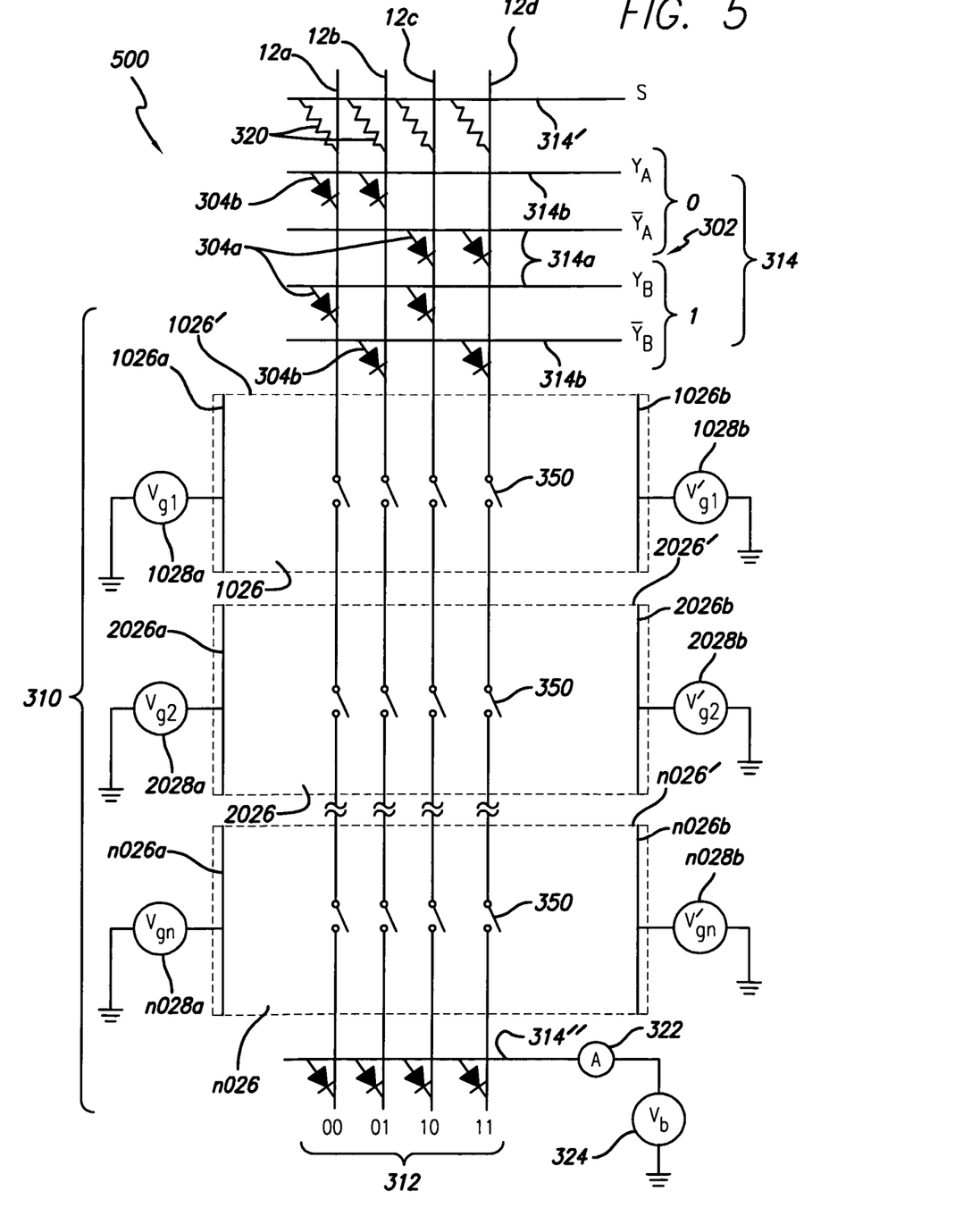
FIG. 5 is similar to FIG. 4, but showing a plurality of gates to permit multiple detection measurements on the same wire at different voltages.

The gated nanosensor array 400 may have more than one gate. FIG. 5 shows an embodiment of a gated nanosensor array 500 with n gates, 1026, 2026, . . . n026. Gate 1026 has sides 1026*a*, 1026*b* under the nanowires, to which different potentials, $V_{g1}$ 1028*a* and $V'_{g1}$ 1028*b*, may be applied. Likewise, gate 2026 has sides 2026*a*, 2026*b* under the nanowires, to which different potentials, $V_{g2}$ 2028*a* and $V'_{g2}$ 2028*b*, may be applied. Likewise, the nth gate, n026 has sides n026*a*, n026*b* under the nanowires, to which different potentials, $V_{gn}$ n028*a* and $V'_{gn}$ n028*b*, may be applied. FIG. 5 allows increased specificity of sensing, compared to FIG. 4, due the presence of additional gates.

FIG. 6 is a diagrammatic view in three dimensions of an embodiment of the gated nanowire sensor array 500', similar to the one shown in FIG. 5. In this embodiment, three gates 1026, 2026, 3026 are shown. Chemical addressing is performed, using the demultiplexer 314 and receptors 120, 220, 320, 420, as described above. Physical tuning is performed via gates 1026, 2026, 3026 and local fields as described above.

The gated nanowire sensor array 500' permits identification of many distinct analytes with one physical nano-array. Here, four analytes may be detected by receptors 120, 220, 320, 420. Any number of analytes may be identified, employing the principles disclosed herein.

The gated nanowire sensor array 500' enables one to fully characterize a multi-dimensional statistical distribution.

Figure 6A:
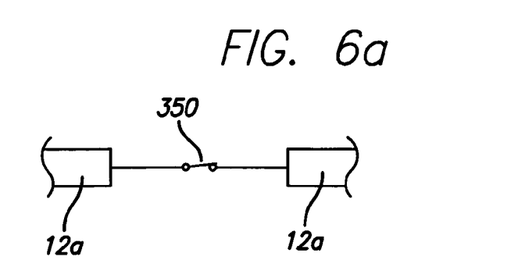
FIGS. 6a and 6b are each a schematic enlargement of a different portion of FIG. 6.
Figure 6B:
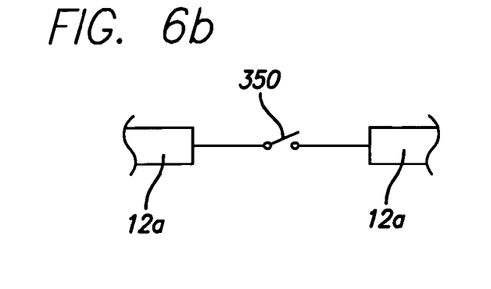

FIGS. 6*a* and 6*b* each schematically show an enlargement of a different portion of FIG. 6. Specifically, FIG. 6*a* depicts a receptor that has not detected an analyte. The resulting switch 350 is a closed switch. Conversely, FIG. 6*b* depicts a receptor that has detected an analyte. The resulting switch 350 is an open switch.

Figure 7:
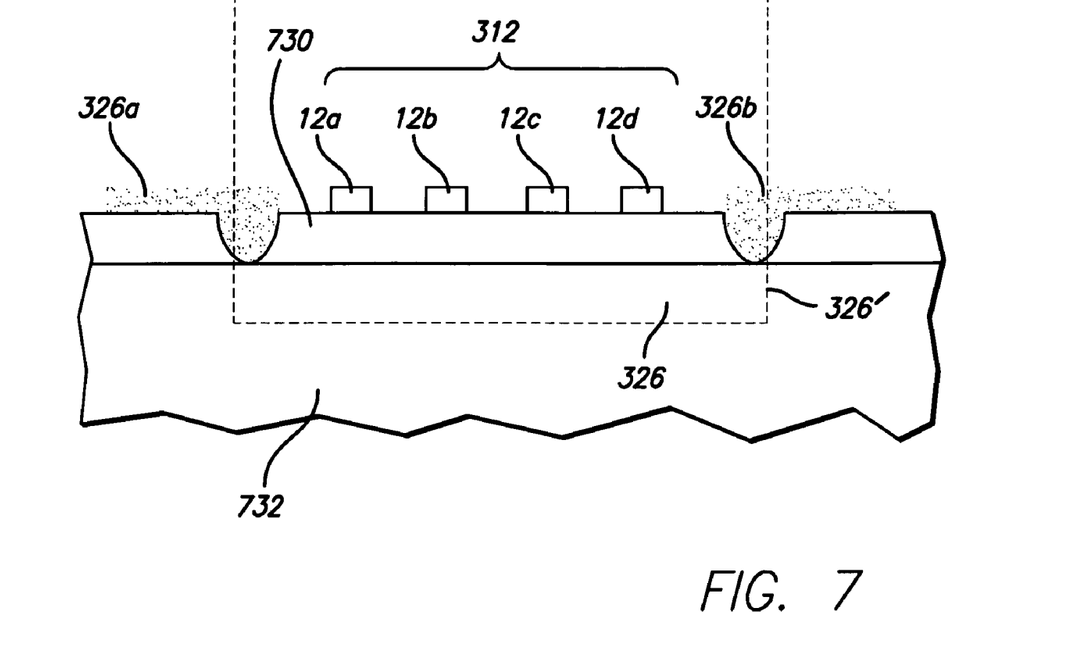
FIG. 7 is a side elevational view, with emphasis on the gated nanowires and the doped Si gate, showing an embodiment of a nanowire sensor array that is gated with a doped Si region underneath a thin insulator.

FIG. 7 shows a side elevational view of a further advantage of the demultiplexed sensor array. As shown in FIG. 7, all of the nanowires 312 can share a single gate 326, which can be fabricated using conventional semiconductor processing techniques. Thus, each nanowire 12*a*, 12*b*, 12*c*, 12*d* becomes a long narrow field-effect transistor (FET). However, by contacting the two opposing edges 326*a*, 326*b* of the gate 326 and by applying different bias voltages to each edge, there is a potential gradient across the nanowire array 312 such that each nanowire has (or experiences) a different gating field. Thus, each nanowire 12*a*, 12*b*, 12*c*, 12*d* in the array 312 will respond differently to an outside stimulus. By examining the dependence of the stimulus as measured by the resistance of each nanowire 12*a*, 12*b*, 12*c*, 12*d* and how that depends on the gating field, an improved ability to differentiate among similar adsorbed species is achieved, or the ability to determined the identity of several different co-adsorbed species is enhanced. By applying a relatively large bias voltage across the gate 326, it also can be used as a heater to thermally desorb molecules from the wires 12*a*, 12*b*, 12*c*, 12*d*. The characteristic temperatures at which various molecules desorb can also be used to help determine the identity of adsorbed species.

With regard to FIG. 7, the side elevational view, with emphasis on the gated nanowires 312 and the doped Si gate 326, shows a nanowire sensor array 310 that is gated with a doped Si region 326 underneath a thin insulator 730, such as silicon dioxide. The doped Si gate 326 is formed in a silicon substrate 732, employing conventional semiconductor processing.

In this case, all of the wires 312 are gated, which makes each wire an FET. The gate voltage allows the sensitivity of the wires 312 to be tuned. This tuning can be used to deplete the nanowires 314 and/or make them respond to different molecular species that adsorb onto the nanowires. By contacting each edge 326a, 326b of the gate 326 under the nanowires 312 and applying different potentials, $V_{g1}$ and $V'_{g1}$, it is also possible to gate each nanowire differently. This makes each nanowire 312 distinct, and therefore reading the state of the different wires provides an additional control that can be used to determine the identity of the adsorbed species. Alternatively, for the case of constant potential on the gate, $V_{g1}$ and $V'_{g1}$ may be the same.

Figure 7A:
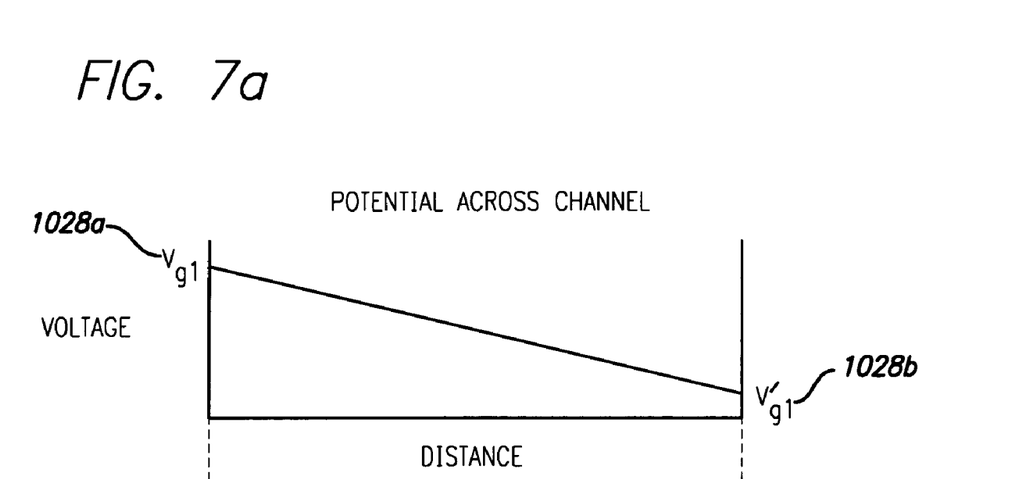
FIG. 7a is a plot, on coordinates of voltage and distance, showing the potential in the doped Si region underneath the nanowires.

FIG. 7a shows that the potential in the doped Si region, or gate, 326 underneath the nanowires 312 varies essentially linearly from $V_{g1}$ to $V'_{g1}$, which means that the gating field under each nanowire is different.

The present teachings allow the fabrication of sensor arrays based on semiconductor wires that both optimize the detection sensitivity of a platform by providing a high density of the wires on the platform surface and also to minimize the expense of building such a system by using a demultiplexer based on diode or resistor logic to select individual nanowires from an array and make a resistance measurement of each wire. This allows examination of the statistics of the adsorption events, which carry information about both the identity of the species being adsorbed and also information about direction of movement. Also, the nanowires can all utilize a single gate with a potential gradient, making each nanowire an FET with different characteristics that can be used for identifying adsorbed species.

What is claimed is:

1. A demultiplexed nanowire sensor array for detecting one or more chemical or biological species, said demultiplexed nanowire sensor array comprising:
    a sensor array, wherein said sensor array comprises (a) a first set of nanowires crossing a second set of nanowires at a non-zero angle to form an array of cross points, (b) an active material between a nanowire of the first set of wires and a nanowire of said second set of wires at a cross point of the array, and (c) a receptor on a portion of the active material at the cross point, electrical properties of said active material at the cross point to be altered by the binding of said species to said receptor, each said receptor specific to detecting a specific chemical or biological species; and
    at least one demultiplexer for addressing said nanowires and permitting measurement of electrical resistance of each said nanowire.

2. The demultiplexed nanowire sensor array of claim 1 wherein at least two cross points are each alterable by a different receptor.

3. The demultiplexed nanowire sensor array of claim 1 wherein said first set of nanowires and said second set of nanowires comprise materials independently selected from the group consisting of metals and semiconductors.

4. The demultiplexed nanowire sensor array of claim 1 wherein said active material is selected from the group consisting of semiconductors, polymers, and molecules.

5. The demultiplexed sensor array of claim 1 wherein said demultiplexer is a diode-logic demultiplexer.

6. A demultiplexed nanowire sensor array for detecting one or more chemical or biological species, said demultiplexed nanowire sensor array comprising:
    a sensor array, wherein said sensor array comprises (a) a set of approximately parallel semiconductor nanowires, (b) at least one gate, said gate crosses said set of nanowires and has a first edge on one side of said set of nanowires and a second edge on another side of said set of nanowires, and (c) each nanowire is functionalized differently from another nanowire;
    a first bias voltage means for applying a first bias voltage to the first edge and a second bias voltage means for applying a second bias voltage to the second edge, the first bias voltage being one of the same as or different from the second bias voltage; and
    at least one demultiplexer for addressing said nanowires and permitting measurement of electrical resistance of each said nanowire.

7. The demultiplexed sensor array of claim 6 wherein said demultiplexer is a diode-logic demultiplexer.

8. The demultiplexed sensor array of claim 6 wherein said demultiplexer is an FET demultiplexer.

9. The demultiplexed sensor array of claim 6 wherein the bias voltage applied to each of the first edge and the second edge is different to create a potential gradient across said set of nanowires and provide each said nanowire with a different gating field.

10. The demultiplexed sensor array of claim 6 wherein said at least one gate may be heated in order to determine characteristic desorption temperatures, in order to aid in identification of said species.

* * * * *